(12) United States Patent
Avery et al.

(10) Patent No.: US 11,090,436 B2
(45) Date of Patent: Aug. 17, 2021

(54) DRUG DELIVERY DEVICE

(71) Applicant: SANOFI, Paris (FR)

(72) Inventors: Richard James Vincent Avery, Gloucestershire (GB); Matthew Meredith Jones, Warwick (GB); William Marsh, Buckinghamshire (GB); Anthony Paul Morris, Coventry (GB); David Aubrey Plumptre, Worcestershire (GB); Samuel Keir Steel, Leamington Spa (GB); Robert Frederick Veasey, Leamington Spa (GB)

(73) Assignee: Sanofi, Paris (FR)

( * ) Notice: Subject to any disclaimer, the term of this patent is extended or adjusted under 35 U.S.C. 154(b) by 611 days.

(21) Appl. No.: 15/557,338

(22) PCT Filed: Mar. 11, 2016

(86) PCT No.: PCT/EP2016/055270
§ 371 (c)(1),
(2) Date: Sep. 11, 2017

(87) PCT Pub. No.: WO2016/142511
PCT Pub. Date: Sep. 15, 2016

(65) Prior Publication Data
US 2018/0050155 A1 Feb. 22, 2018

(30) Foreign Application Priority Data
Mar. 12, 2015 (EP) ..................... 15305380

(51) Int. Cl.
A61M 5/20 (2006.01)
A61M 5/315 (2006.01)
(Continued)

(52) U.S. Cl.
CPC ............ *A61M 5/20* (2013.01); *A61M 5/3157* (2013.01); *A61M 5/31541* (2013.01);
(Continued)

(58) Field of Classification Search
CPC .......... A61M 5/31541; A61M 5/31553; A61M 5/3157; A61M 5/31583; A61M 5/31593;
(Continued)

(56) References Cited

U.S. PATENT DOCUMENTS 7,749,186 B2 7/2010 Kohlbrenner et al.
8,052,655 B2 11/2011 Moller et al.
(Continued)

FOREIGN PATENT DOCUMENTS

CN 1607969 4/2005
CN 101681421 3/2010
(Continued)

OTHER PUBLICATIONS

International Preliminary Report on Patentability in International Application No. PCT/EP2016/055270, dated Sep. 12, 2017, 7 pages.
(Continued)

*Primary Examiner* — Theodore J Stigell
(74) *Attorney, Agent, or Firm* — Fish & Richardson P.C.

(57) ABSTRACT

The present disclosure is generally directed to a drug delivery device for selecting and dispensing a number of user variable doses of a medicament. The device comprises a housing and at least two separate component parts, wherein for example at least one of these component parts performs a movement relative to the housing during dose setting and for example at least one of these component parts performs a movement relative to the housing during dose dispensing, and wherein the relative movement of the at least two separate component parts with respect to each other during
(Continued)

dose setting differs from the relative movement of the at least two separate component parts with respect to each other during dose dispensing. The device further comprises a monitoring device, wherein at least one component part of the device is diaphanous to allow optical detection of the movements of the at least two separate component parts relative to the housing, relative to the monitoring device and/or relative to each other during dose setting and/or during dose dispensing by the monitoring device.

21 Claims, 3 Drawing Sheets

(51) Int. Cl.
*A61M 5/24* (2006.01)
*A61M 5/31* (2006.01)

(52) U.S. Cl.
CPC .... *A61M 5/31553* (2013.01); *A61M 5/31583* (2013.01); *A61M 5/31593* (2013.01); *A61M 2005/2407* (2013.01); *A61M 2005/3126* (2013.01); *A61M 2205/3306* (2013.01); *A61M 2205/50* (2013.01); *A61M 2205/581* (2013.01); *A61M 2205/582* (2013.01); *A61M 2205/583* (2013.01)

(58) Field of Classification Search
CPC .. A61M 2005/2407; A61M 2005/3126; A61M 5/31568
See application file for complete search history.

(56) References Cited

U.S. PATENT DOCUMENTS

| | | | |
|---|---|---|---|
| 8,197,449 B2 | 6/2012 | Nielsen et al. |
| 8,231,573 B2 | 7/2012 | Edwards et al. |
| 8,556,847 B2 | 10/2013 | Kohlbrenner et al. |
| 8,556,865 B2 | 10/2013 | Krulevitch et al. |
| 8,556,866 B2 | 10/2013 | Krulevitch et al. |
| 8,556,867 B2 | 10/2013 | Krulevitch et al. |
| 8,560,271 B2 | 10/2013 | Koehler et al. |
| 8,613,719 B2 | 12/2013 | Karratt et al. |
| 8,672,899 B2 | 3/2014 | Diller et al. |
| 8,771,238 B2 | 7/2014 | Nielsen et al. |
| 8,994,382 B2 | 3/2015 | Nielsen et al. |
| 9,289,559 B2 | 3/2016 | Pedersen et al. |
| 9,522,238 B2 | 12/2016 | Nielsen et al. |
| 9,526,842 B2 | 12/2016 | Oh et al. |
| 9,623,188 B2 | 4/2017 | Nielsen et al. |
| 9,649,448 B2 | 5/2017 | Madsen |
| 9,672,328 B2 | 6/2017 | Saint et al. |
| 9,734,302 B2 | 8/2017 | Nielsen et al. |
| 9,959,391 B2 | 5/2018 | Saint et al. |
| 10,105,489 B2 | 10/2018 | Edwards et al. |
| 10,213,554 B2 | 2/2019 | Andersen et al. |
| 10,383,996 B2 | 8/2019 | Miller et al. |
| 10,483,000 B2 | 11/2019 | Saint et al. |
| 10,593,232 B2 | 3/2020 | Bauss |
| 10,617,827 B2 | 4/2020 | Hautaviita et al. |
| 10,695,504 B2 | 6/2020 | Nielsen et al. |
| 10,857,304 B2 | 12/2020 | Byerly |
| 2008/0234633 A1* | 9/2008 | Nielsen .................. A61M 5/24 604/208 |
| 2014/0005950 A1 | 1/2014 | Groeschke et al. |
| 2014/0194825 A1 | 7/2014 | Nielsen et al. |
| 2015/0343152 A1* | 12/2015 | Butler ............... A61M 5/31551 604/207 |

FOREIGN PATENT DOCUMENTS

| | | |
|---|---|---|
| CN | 103717247 | 4/2014 |
| CN | 104203318 | 12/2014 |
| EP | 0751865 | 1/1997 |
| JP | 2004-526486 | 9/2004 |
| JP | 2014-516599 | 7/2014 |
| JP | 2014-520584 | 8/2014 |
| WO | WO 95/26869 | 10/1995 |
| WO | WO 2002/064196 | 8/2002 |
| WO | WO 2009/015933 | 2/2009 |
| WO | WO 2012/127046 | 9/2012 |
| WO | WO 2013/004844 | 1/2013 |
| WO | WO 2013/010889 | 1/2013 |
| WO | WO 2013/120778 | 8/2013 |
| WO | WO 2014/111339 | 7/2014 |
| WO | WO 2014/111340 | 7/2014 |
| WO | WO 2014/113340 * | 7/2014 |
| WO | WO 2016/001300 | 1/2016 |
| WO | WO 2016/142511 | 9/2016 |
| WO | WO 2019/173097 | 9/2019 |

OTHER PUBLICATIONS

International Search Report and Written Opinion in International Application No. PCT/EP2016/055270, dated Jun. 24, 2016, 10 pages.

* cited by examiner

DRUG DELIVERY DEVICE

CROSS REFERENCE TO RELATED APPLICATIONS

The present application is the national stage entry of International Patent Application No. PCT/EP2016/055270, filed on Mar. 11, 2016, and claims priority to Application No. EP 15305380.6, filed in on Mar. 12, 2015, the disclosures of which are expressly incorporated herein in entirety by reference thereto.

TECHNICAL FIELD

The present disclosure is generally directed to a drug delivery device for selecting and dispensing a number of user variable doses of a medicament. The device comprises a housing and at least two separate component parts, wherein at least one of these component parts performs a movement relative to the housing or further a component part, e.g. a button, during dose setting, at least one of these component parts performs a movement relative to the housing during dose dispensing, and wherein the relative movement of the at least two separate component parts with respect to each other during dose setting differs from the relative movement of the at least two separate component parts with respect to each other during dose dispensing.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

BACKGROUND

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

Especially for visually impaired users it is helpful to have a non-visual feedback during operation of the device. This may include a feedback generated during dose setting, a feedback generated during dose correction, a feedback generated during dose dispensing and/or a feedback generated at the end of dose dispensing. A non-visual feedback signal may be an audible and/or tactile feedback signal.

A drug delivery device with a clicker mechanism active during dose dispensing is described in the unpublished European patent application "Drug Delivery Device", filed on Jul. 1, 2014 by the same applicant, currently pending as EP 14 306 065.5. The drug delivery device comprises a dose setting member (number sleeve) rotatable during dose setting and dose dispensing and a driver which is coupled to the dose setting member by a clutch mechanism such that relative rotation of the driver and the dose setting member is allowed during dose setting and that relative rotation of the driver and the dose setting member is prevented during dose dispensing.

After the injection is complete, i.e. after dose dispensing has been performed by the drug delivery device, a user of the device is typically instructed to continue pressing the dispense button or trigger for a period of time known as "dwell period", for example for 10 seconds. This allows internal forces in the mechanism to relax, in particular any compression within the bung of the cartridge, and so ensures that the complete dose is delivered.

SUMMARY

It is an object of the present disclosure to provide a drug delivery device as defined above which allows indication of a condition to a user, for example the end of the dwell period.

This object is solved by a device as defined in claim 1. According to the present disclosure the device comprises a monitoring device to allow detection of the movements of component parts relative to the housing and/or relative to the monitoring device during dose setting and during dose dispensing by the monitoring device. Preferably, at least one component part of the device is diaphanous, i.e. transparent or translucent, comprises a transparent area within the part, an overlabeled area, a door, or hole within the part to allow optical detection of the movements of component parts. As an alternative to an optical detection, detection methods may include contact or audio methods of movement detection.

In other words, an electronic device is provided which can be attached to the injector mechanism, e.g. onto the button of the drug delivery device. The electronic monitoring device views/detects internal parts of the mechanism to read, and optionally display, information about the state of the mechanism, for example the size of the dialed dose, and whether the mechanism is at rest, dialing a dose, or dispensing a dose. Viewing/detecting internal parts of the drug delivery device is possible due to one or more diaphanous component parts or at least a diaphanous portion thereof. For example, a component part may be completely transparent, may comprise a transparent window, may comprise an aperture and/or may be modified in another appropriate manner allowing optical detection of one or more component parts. Preferably, the monitoring device is a dwell timer which may determine when injection is complete, count the time until the dwell period is complete, and provide a feedback to a user.

According to an embodiment of the disclosure, a drug delivery device for selecting and dispensing a number of user variable doses of a medicament comprises a housing, a monitoring device with an e.g. optical detector, a data processor and at least one output member, and at least one component part which moves relative to the monitoring device during dose setting and/or during dose dispensing, wherein the data processor is configured as a dwell timer suitable for outputting optical, tactile and/or audible feedback to a user of the drug delivery device via the at least one output member at a predefined time span after the optical sensor detects the end of movement of the at least one component part. For example, the monitoring device may detect at least one part, e.g. the dose setting member, that rotates relative to the monitoring device during dispense but not during dialing. Alternatively, the monitoring device may detect at least two parts, e.g. the dose setting member and the driver, where relative movement during dose setting differs from relative movement during dose dispensing. If the monitoring device uses optical detection, one or more of the parts may be provided with a hole and/or may be fully or partially transparent or translucent. The monitoring device may be releasably attached to the housing.

The monitoring device may display the size of the dialed dose, indicate whether the injector is dialing or dispensing, and during dispense it may show the size of the remaining dose. It may also store a history of the size and time of doses that have been dispensed, and display them on the screen or allow downloading of data to an external device.

Another independent aspect of the present disclosure is the transparency of plastic component parts in a drug delivery device configured for allowing optical monitoring of an action, a movement and/or a state of the device. This is especially useful for a device comprising a dwell timer, i.e. an electronic component part indicating the end of the dwell period by a feedback signal.

The dwell timer detects whether the drug delivery device is at rest, i.e. in a state or condition with no dose set and no external force applied to a button or trigger, dialing a dose, i.e. increasing or decreasing the set dose, or dispensing a dose by monitoring movements, in particular rotation, of internal parts relative to the housing and/or relative to the monitoring device itself. In order to do this, it needs to view two parts that have a different behaviour from each other during dialing (dose setting) and injecting (dose dispensing).

Generally, the monitoring device may detect and monitor movements of various component parts. For example, the at least two separate component parts which are viewed by the monitoring device may comprise a lead screw, a driver, a dose setting member (number sleeve), a button or trigger, a dial grip, a spring, a gauge element and/or a clutch. The monitoring device may detect different kinds of movements including rotation and linear displacement. In an embodiment of the disclosure, the at least two separate component parts are the dose setting member, which is rotatable relative to the housing during dose setting and during dose dispensing, and the driver, which is rotationally constrained to the housing during dose setting and rotatable together with the dose setting member during dose dispensing. In other words, the dwell timer monitors rotation of the dose setting member, e.g. a number sleeve, and the driver, e.g. a drive sleeve located at least partially within the dose setting member. These two component parts are both stationary when at rest. During dialing, the dose setting member rotates relative to the housing and, for example together with the button onto which the monitoring device may be attached, while the driver is still stationary. During dispensing, the dose setting member and the driver rotate together relative to the housing, wherein the button with the monitoring device may be rotationally constrained to the stationary housing during dispensing.

In other embodiments of the disclosure, the monitoring device or dwell timer may monitor other parts that rotate relative to the monitoring device, for example the housing and/or the clutch plate. Alternatively, the dwell timer may be fixed to the housing and so monitor parts that rotate or displace relative to the housing, for example the button, the dial grip, the driver, the lead screw, the number sleeve, the gauge element and/or the clutch plate. As a further alternative, the dwell timer may monitor only one single component part that rotates relative to the monitoring device during dispensing but not during dialing, for example the dose setting member. This does not allow reading of a dialed dose but allows measuring of any dose that is delivered.

The diaphanous component part may comprise a lead screw, a driver, a dose setting member, a button, a dial grip, a spring, a gauge element and/or a clutch. In an embodiment of the disclosure, the diaphanous component part is the button and/or the clutch plate interposed between the dose setting member and the driver. For example, the clutch plate may be permanently rotationally constrained to the dose setting member. Further, the button or trigger may be rotatable (rotationally constrained to the dose setting member) relative to the housing during dose setting, but rotationally constrained to the stationary housing during dose dispensing, while being rotationally decoupled from the dose setting member.

Monitoring the movements of the component parts may require that the component parts have a shape or configuration that allows detecting whether the parts move or not. For example, one or more of the component parts may have a non-circular rotation indicator portion, like a notched or toothed portion, preferably facing towards the monitoring device. This may provide a change in color, darkness, contrast and/or reflectivity during movement of the respective component part when viewed by the monitoring device. In addition or as an alternative, one or more of the component parts may have an optically detectable, e.g. non-symmetric, surface coding, like a non-symmetrical surface color interfering with a complementary pattern on a further component part.

The at least one diaphanous component part may be transparent or translucent for visible light. As an alternative, the at least one diaphanous component part may be opaque for visible light but transparent or translucent for invisible light. For example, it may be desirable to provide a device with a housing and/or button having the usual opaque appearance to a user, while allowing detection of movements of parts housed or shielded by the housing and/or button. An example is a housing or button being transparent only for infrared light. Component parts having a different transmission and absorption coefficient from one another for the spectrum of laser beams are described in EP 0 751 865 B1 to which reference is made regarding spectral selective transparency for an opaque appearance.

In particular if the drug delivery device is a disposable device, the monitoring device may be releasably attached to the housing and/or to at least one further component part of the drug delivery device, like a button or trigger. For example, the monitoring device may comprise hooks or deflectable arms for snapping or clipping the monitoring device onto the button. As an alternative, the monitoring device may be permanently attached to the device.

The monitoring device may be an electronic device which comprises an optical detector, a data processor and at least one output member for providing an optical, tactile (for example vibration) and/or audible feedback to a user of the drug delivery device. As well as this feedback or instead of it, the monitoring device may display the size of the dialed dose, may indicate whether the drug delivery device is dialing or dispensing, and/or during dispensing it may show the size of the remaining dose. Further, it may store a history of the size and/or time of doses that have been dispensed, and may display them on a screen and/or allow downloading of data to an external device.

In an embodiment of the disclosure, the monitoring device is configured for monitoring one or more of the following motions:
 a) rotation of the dose setting member relative to the monitoring device and/or relative to the housing during dose setting and/or dose dispensing,
 b) rotation of the driver relative to the monitoring device and/or relative to the housing during dose setting and/or dose dispensing,
 c) rotation of the dose setting member relative to the driver during dose setting and/or dose dispensing,
 d) return of the dose setting member and/or the driver to an at rest position,
 e) rotation of the button relative to the monitoring device and/or relative to the housing during dose setting and/or dose dispensing,
 f) rotation of the lead screw, the clutch (or clutch plate) and/or the dial grip relative to the monitoring device and/or relative to the housing during dose setting and/or dose dispensing.

Preferably, the data processor is configured as a dwell timer suitable for outputting the optical, tactile and/or audible feedback to a user of the drug delivery device via the at least one output member at a predefined time span after detection of the end of at least one of the above mentioned motions. In addition or as an alternative, the monitoring device may be configured for detecting button pressure exceeding a dose dispensing start threshold.

Further, the monitoring device may be configured to provide a user with a feedback signal at the end of dose dispensing, in a dose dispensing aborting or blocking condition, and/or when dose dispensing starts with an overdose or underdose dial setting.

The drug delivery device may be a spring driven device. In a preferred embodiment, the drive spring may be pre-strained and/or may be strained (charged) during dose setting. The drive spring may be attached at one end to the housing component and/or an additional housing component and at the other end to a component part coupled to a dose setting member, e.g. the number sleeve. The torsion spring may be pre-wound upon assembly of a drug delivery device, such that it applies a torque to the mechanism when the mechanism is at zero units dialed.

Providing a resilient drive member, such as a torsion spring, generating the force or torque required for dose dispensing reduces the user applied forces for dose dispensing. This is especially helpful for users with impaired dexterity. In addition, the dial extension of the known manually driven devices, which is a result of the required dispensing stroke, may be omitted by providing the resilient member because merely a small triggering stroke may be necessary for releasing the resilient member.

The torsion spring may be formed from a helical wire with at least two different pitches. Preferably, both ends are formed from 'closed' coils, i.e. the pitch equals the wire diameter and each coil contacts the adjacent coil, while the central portion has 'open' coils, i.e. the coils do not contact each other.

Having both open and closed coils in the spring has the following advantages: When a dose is set, the torsion spring is usually charged. If all the coils were closed, winding up the spring would increase the length of the spring by one wire diameter for each turn, and so hook ends of the spring would no longer be aligned with their anchor points, which are e.g. on the number sleeve and the housing. The open coils allow the spring to compress to accommodate the additional turns of wire, without increasing the total length of the spring. Further, the open coils allow the spring to be compressed during assembly. For example, the spring is manufactured longer than the space available in the device. It is then compressed during assembly, ensuring that the axial positions of the hook ends are better aligned with their anchor points on the housing and the number sleeve. In addition, it is easier to manufacture the spring to a specified length if most of the coils are closed, as the length of these coils is only a function of the wire diameter. Including at least one open coil allows the spring to be compressed during assembly, which biases the number sleeve axially relative to the housing in a consistent direction, reducing the effects of geometric tolerances. The addition of closed coils at each end makes the springs less prone to tangling with each other when they are stored together between manufacture and assembly. Closed coils at the ends provide a flat surface for contact with the housing and number sleeve which is preferred.

According to a preferred embodiment the button is axially displaceable between a dose setting position and a dose dispensing position, wherein the button is rotatable relative to the housing in its dose setting position and rotationally locked to the housing in its dose dispensing position. A dispense clicker may be provided by ratchet features of the button and a clicker arm of the clutch plate. Thus, the clicker feedback signal is not generated during dose setting (or dose correction) but only during dose dispensing, when relative rotation between the (fixed) button and the (rotating) clutch element occurs. Rotationally constraining the button to the housing during dose dispensing has the additional advantage that there is no friction due to relative rotation between a users finger and the button. Further, this prevents unintended manipulation of the set dose during dispensing.

If the button is rotatable relative to the number sleeve in its dose dispensing position and rotationally locked to the number sleeve in its dose setting position, relative rotation between the button and the clutch element which is constrained to the number sleeve occurs during dose dispensing but not during dose setting. This allows generating different feedback signals during dose setting and dose dispensing.

In a preferred embodiment of the disclosure the clutch element is axially biased in abutment with the button by a clutch spring such that the button axially displaces the clutch element when displaced into its dose dispensing position and that the clutch element axially displaces the button into its dose setting position. Thus, the clutch spring holds the button in its dose setting position if no external force is exerted to the button. Preferably, the drive sleeve is axially movable together with the button and the clutch element between a dose setting position and a dose dispensing position.

The drive sleeve may be coupled to the button via the clutch element such that upon actuation of the button the drive sleeve and the clutch element are translated against the bias of the clutch spring from a proximal position in which the drive sleeve is rotationally locked to the housing into a distal position in which the drive sleeve is rotationally un-locked from the housing, and wherein upon release of the button the clutch spring translates the drive sleeve, the clutch element and the button into the proximal position.

The clutch spring may bias clutch features of the clutch element and the drive sleeve into engagement. Preferably, the clutch features together form a releasable ratchet clutch suitable to couple and de-couple the drive sleeve and the clutch element. For example the clutch features may be rotationally constrained when engaged and free to rotate relative to each other when disengaged. The disengaged state of the corresponding clutch features may include a condition where the clutch features contact each other, but are allowed to overhaul each other, i.e. the corresponding clutch features slip. Further, this ratchet clutch interface may be designed, e.g. by providing meshing ratchet teeth on the drive sleeve and on the clutch element, such that relative rotation of the drive sleeve and the number sleeve requires a relatively low force or torque in one direction, preferably the dose setting direction, and requires a significantly higher force or torque in the opposite direction, preferably the dose correction direction. For example, in the dose setting direction, a shallow ramp reduces the torque but winding up the spring increases the torque, while in the dose correction direction, a steep ramp increases the torque but unwinding the spring reduces the torque. Thus, the torque for dose correction and dose dialing may therefore be equal, but one may be larger than the other. As an alternative, the ratchet features may be designed to allow relative rotation of the drive sleeve and the number sleeve only in one direction, typically the dose setting direction, while fully preventing relative rotation of the drive sleeve and the number sleeve only in the opposite direction.

In a preferred embodiment the number sleeve and the drive sleeve are allowed to rotate relative to each other when the drive sleeve is in its first axial position and are rotationally constrained when the drive sleeve is in its second axial position. In the drug delivery device, the first axial position may be a dose setting position and the second axial position may be dose dispensing position.

In addition to the dispense clicker, a feedback signal may be provided during dose setting and/or dose correction. Preferably, the ratchet clutch formed by teeth on the drive sleeve and the clutch element generate an audible and/or tactile feedback signal upon relative rotation of the clutch element with respect to the drive sleeve during dose setting and/or dose correction. This feedback signal may be distinct from the dispense clicker signal.

The clutch features may be in a releasable engagement allowing the clutch features to be overhauled against the bias of the clutch spring at least in one rotational direction when the drive sleeve is in the proximal position and that the clutch features are rotationally constrained when the drive sleeve is in the distal position. For example, the clutch features may each comprise a series of teeth, preferably saw-teeth, which are allowed to slip over each other if not pressed against each other too firmly. In other words, the clutch features may be overhauled against the bias of the clutch spring by allowing the drive sleeve and/or the clutch element to translate axially against the force of the clutch spring. This may result in an oscillating axial movement of the drive sleeve and/or the clutch element due to continued disengagement and following re-engagement into the next detented position. An audible click may be generated by this re-engagement, and tactile feedback may be given by the change in torque input required.

In addition, the clutch features preferably comprise teeth having a ramp angle allowing overhauling of the ratchet, e.g. for dose correction. In other words, relative rotation of the drive sleeve and the clutch element is allowed in both directions when the clutch arrangement is in the state or condition where the clutch features and the corresponding clutch features are not rotationally fixed.

Preferably, the clutch features provides a detented position between the drive sleeve and the clutch element corresponding to each dose unit, and engage different ramped tooth angles during clockwise and anti-clockwise relative rotation. This is especially useful if the device further comprises a drive spring having a force or torque which is reacted via the clutch features from the clutch element and the drive sleeve to the housing. The drive spring may be directly or indirectly coupled to the clutch element.

A further feedback signal may be provided as an end of dose dispensing indication. Preferably, the drug delivery device further comprises a clicker arrangement having a clicker arm on the number sleeve, a ramp on the drive sleeve and a cam on a further element, e.g. a gauge element, wherein upon relative rotation of the number sleeve and the gauge element the clicker arm is elastically deflectable by the cam and relaxable upon disengagement with the cam thereby generating an audible and/or tactile feedback signal. When the drive sleeve is in a first axial position, the ramp preferably does not interact with the clicker arm which in turn prevents the clicker arm from contacting the cam, and when the drive sleeve is in a second axial position, the ramp deflects the clicker arm such that the clicker arm contacts the cam. The number sleeve and the gauge element may be in threaded engagement. Thus, the gauge element is axially displaced upon relative rotation of the number sleeve. This allows engagement and dis-engagement of the cam and the clicker arm depending on the relative axial position of the cam and the clicker arm.

With respect to the feedback signal generated at the end of dose dispensing, it is an important aspect of the present disclosure that the clicker arrangement comprises a first, rotatable element and a second, non-rotatable element with one of the first element and the second element comprising a clicker arm, which is elastically deformable, and the other of the first element and the second element comprising a cam. Upon relative rotation of the first element and the second element the clicker arm is elastically deflected by the cam and relaxes upon disengagement with the cam thereby generating an audible and/or tactile feedback signal. The present disclosure includes the idea of further providing a third, axially movable element having a ramp which interacts with the clicker arm at least in a defined position of the third element. In more detail, the ramp does not interact with the clicker arm which in turn prevents the clicker arm from contacting the cam when the third element is in a first axial position. However, when the third element is in a second axial position, the ramp deflects the clicker arm such that the clicker arm contacts the cam. In other words, the clicker arrangement may be activated to generate the feedback signal by bringing the third element in its second position and may be de-activated preventing generation of a signal by bringing the third element in its first position. This allows the feedback signal to be produced only in a defined mode, typically during dose dispensing when used in a drug delivery device. The feedback signal generated by the clicker arrangement is preferably distinct from other signals which may be generated in a drug delivery device, for example a visual indication and/or an audible and/or tactile feedback signal generated during dose setting, dose correction and/or dose dispensing. Dose correction is understood to be reducing an already set dose without dispensing medicament.

According to the present disclosure the cam preferably does not contact the clicker arm when the third element is in its first axial position, which is when used in a drug delivery device preferably if a trigger or actuation button is in a not depressed 'at rest' condition. Thus, during storage or dialing the clicker arm is not deflected and will not suffer creep deformation. In addition the clicker arrangement does not cause friction losses during dialing or dose correction which contributes to a user-friendly device requiring only low dialing force or torque.

During dialing (dose setting), the second element may translate, e.g. in the proximal direction, so the cam is no longer aligned axially with the clicker arm. Preferably, at the start of dose delivery when the third element translates in the distal direction, the ramp on the third element pushes the clicker arm for example radially outwards. During dose delivery, the second element may translate back in the distal direction, and towards the end of dose delivery, the clicker arm contacts the cam. Only in this position is generation of the feedback signal possible. For small doses, the cam and the clicker arm may be in contact at the start of dose dispensing. After dose delivery, the trigger or button is typically released and the clicker arrangement returns to its 'at rest' position.

Preferably, the element comprising the clicker arm is a tubular element with the clicker arm being deflectable radially inwards and outwards. The third element comprising the ramp is preferably arranged radially inwards of the element comprising the clicker arm such that the ramp is able to push the clicker arm radially outwards. The element comprising the cam may be arranged radially outwards of the element comprising the clicker arm such that the cam is able to push the clicker arm radially inwards.

There are various ways of generating the audible and/or tactile feedback signal by any of the clicker arrangements of the present disclosure. For example, the audible and/or tactile feedback signal may be generated by disengagement of a clicker arm and a tooth or a cam. In other words, the signal is caused e.g. by the pre-tensioned clicker arm falling off an edge of the tooth or cam. As an alternative, the audible and/or tactile feedback signal may be generated by contact of a first portion of the clicker arm with the tooth or cam after disengagement of a second portion of the clicker arm with the tooth or cam. For example, the second portion of the clicker arm, e.g. a lever portion, may hit the tooth or cam after the first portion of the clicker arm, e.g. a projecting tip of the arm, disengages or loses contact with the tooth or cam. In an embodiment comprising a cam it is preferred if the element with the cam further comprises a recess for receiving the second portion, e.g. the tip, of the clicker arm after disengagement of the second portion of the clicker arm with the cam.

The clutch element comprises the corresponding clutch features and may have the form of a plate or disk. As an alternative, the clutch element may have the form of a sleeve. The clutch element is axially interposed between the sleeve and the button such that axial movement of the button in a first direction, preferably in the distal direction, is transferred to the sleeve via the clutch element and axial movement in the opposite, preferably proximal, direction is transferred to the button via the clutch element. As an alternative, the clutch element may be a unitary part of the button. In a preferred embodiment the clutch element is permanently or releasably coupled to further component parts of a drug delivery device, for example a number sleeve and/or a dose setting member. The clutch element may be a multi-functional element having in addition to the interface with the sleeve and the interface with the button e.g. a clicker feature and/or at least one further interface.

The button is preferably a user operable element located proximally from the sleeve and the clutch element. When used in a drug delivery device, the button may extend from the proximal end of the device and, preferably, does not change its axial position during dose setting. The button is preferably coupled to a user operable dose setting member and may be releasably coupled to a number sleeve component and/or a stationary housing component. In an alternative embodiment, the button may be part of a dose setting arrangement or may be the dose setting member. The button is a multi-functional element having in addition to the above features the clicker feature.

The stationary housing component is a fixed basis for relative movements of the axially movable sleeve, the clutch element and the button. It may be part of a multi-component housing or may be the only housing component of a drug delivery device. In a preferred embodiment, the stationary housing component comprises an axial support or bearing for the clutch spring and means for releasably engaging the sleeve. Preferably, the housing component comprises one or more teeth, for example a ring of teeth, engaging one or more corresponding teeth, preferably also a ring of teeth, of the sleeve depending on the relative axial position of the sleeve with respect to the housing component. In other words, the engagement means or teeth mesh and interlock in a first, e.g. proximal, position of the sleeve relative to the housing component and are disengaged, thus allowing relative rotation, in a second, e.g. distal, position of the sleeve relative to the housing component. The housing component may be a multi-functional element having in addition to the above features e.g. a clicker feature and/or an interface to a piston rod.

The axially movable drive sleeve is a tubular element which has, preferably at its distal end, an interface for releasable engagement with the housing component and, preferably at its proximal end, an interface for releasable engagement with the clutch element, namely the clutch features. Preferably, the drive sleeve is rotationally constrained to the piston rod which is in threaded engagement with the stationary housing part. In other words, rotation of the drive sleeve relative to the housing component causes rotation of the piston rod and, thus, axial displacement of the piston rod relative to the housing component. This may be used in a drug delivery device during dose dispensing to advance a piston in a cartridge to expel medication from the cartridge. The drive sleeve may be a multi-functional element having in addition to the above features e.g. a clicker feature and/or an activation interface for a clicker.

In a drug delivery device at least one dose setting member may be provided operable to set a dose, wherein actuation of the button causes dispensing of the set dose. Preferably, the operation of the at least one dose setting member strains the drive spring and actuation of the button allows the drive spring to relax and thereby rotate the clutch element, the drive sleeve and the piston rod relative to the housing component which causes the piston rod to advance in the distal direction relative to the housing component.

The drug delivery device may comprise the housing, having the first aperture, the number sleeve positioned within the housing and rotatable with respect to the housing during dose setting and during dose dispensing, and the gauge element, which is interposed between the housing and the number sleeve. Preferably, the gauge element has a second aperture, which is positioned with respect to the first aperture of the housing such that at least a part of the number sleeve is visible through the first and second apertures. The gauge element may be axially guided within the housing and in threaded engagement with the number sleeve such that rotation of the number sleeve causes an axial displacement of the gauge element.

The position of the gauge element may thus be used to identify the actually set and/or dispensed dose. Different colours of sections of the gauge member may facilitate identifying the set and/or dispensed dose without reading numbers, symbols or the like on a display. As the gauge element is in threaded engagement with the number sleeve, rotation of the number sleeve causes an axial displacement of the gauge element relative to the number sleeve and relative to the housing. The gauge element may have the form of a shield or strip extending in the longitudinal direction of the device. As an alternative, the gauge element may be a sleeve. In an embodiment of the disclosure, the number sleeve is marked with a sequence of numbers or symbols and the gauge element comprises an aperture or window. With the number sleeve located radially inwards of the gauge element, this allows that at least one of the numbers or symbols on the number sleeve is visible through the aperture or window. In other words, the gauge element may be used to shield or cover a portion of the number sleeve and to allow viewing only on a limited portion of the number sleeve. This function may be in addition to the gauge element itself being suitable for identifying or indicating the actually set and/or dispensed dose.

In a preferred embodiment, the number sleeve, during dose setting, is adapted to undergo a mere rotational movement within the housing and relative to the housing. In other words, the number sleeve does not perform a translational movement during dose setting. This prevents the need for the number sleeve to be wound out of the housing or for the housing to be prolonged for covering the number sleeve within the housing.

It is preferred if the device is suitable for dispensing variable, user-selectable, doses of medicament. The device may be a disposable device, i.e. a device which does not provide for an exchange of an empty cartridge.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to reduce the risk of overdosage and to avoid the additional spring torque needed for dispensing very high doses, while still being suitable for a wide range of patients needing different dose sizes. Preferably, the limits for the minimum dose and the maximum dose are provided by hard stop features. The limiter mechanism may comprise a first rotational stop on the number sleeve and a first counter stop on the gauge element, which abut in the minimum dose (zero) position, and a second rotational stop on the number sleeve and a second counter stop on the gauge element, which abut in the maximum dose position. As the number sleeve rotates relative to the gauge element during dose setting and during dose dispensing, these two components are suitable to form a reliable and robust limiter mechanism.

The drug delivery device may further comprise a last dose protection mechanism for preventing the setting of a dose, which exceeds the amount of liquid left in a cartridge. This has the advantage that the user knows how much will be delivered before starting the dose delivery. It also ensures that dose delivery stops in a controlled manner without the bung entering the neck portion of the cartridge where the diameter is smaller which may result in an underdose. In a preferred embodiment, this last dose protection mechanism only detects the medicament remaining in the cartridge when the cartridge contains less than the maximum dose (e.g. 120 IU). For example, the last dose protection mechanism comprises a nut member interposed between the drive member and a component which rotates during dose setting and dose dispensing. The component which rotates during dose setting and dose dispensing may be the number sleeve or a dial sleeve rotationally constrained to the number sleeve. In a preferred embodiment, the number sleeve and/or a dial sleeve rotate during dose setting and during dose dispensing, whereas the drive member only rotates during dose dispensing together with the number sleeve and/or the dial sleeve. Thus, in this embodiment, the nut member will only move axially during dose setting and will remain stationary with respect to these components during dose dispensing. Preferably, the nut member is threaded to the drive member and splined to the number sleeve and/or the dial sleeve. As an alternative, the nut member may be threaded to the number sleeve and/or the dial sleeve and may be splined to the drive member. The nut member may be a full nut or a part thereof, e.g. a half nut.

A further aspect of the present disclosure is the provision of several interfaces on the axially movable drive sleeve. Preferably, the drive sleeve has a first interface for permanently rotationally constraining the drive sleeve and the lead screw. A second interface may be provided between the drive sleeve and the housing (or a housing component) for rotationally constraining the drive sleeve and the housing depending on the axial position of the drive sleeve. A third interface may be provided between the drive sleeve and the number sleeve (or a dose setting component) for rotationally constraining the drive sleeve and the number sleeve depending on the axial position of the drive sleeve. A fourth interface may be provided between the drive sleeve and the clutch element for rotationally constraining the drive sleeve and the clutch element depending on the axial position of the drive sleeve and/or the bias of the clutch spring. A fifth interface may be provided between the drive sleeve and the number sleeve or the gauge element for generating a feedback signal upon rotation of the drive sleeve, preferably only at the end of dose dispensing, and depending on the axial position of the drive sleeve.

Further, the drug delivery device may comprise a second clutch rotationally coupling the actuation button to the number sleeve when the actuation button and the drive sleeve are in the first dose setting position and de-coupling the actuation button from the number sleeve when the actuation button and the drive sleeve are in the second dose dispensing position. In a preferred embodiment a releasable interface between the housing and the button is provided by e.g. splines engaging with the housing to prevent rotation of the button and hence the dose selector during dispense.

Preferably, the piston rod (lead screw) advances by a fixed displacement for each revolution of the movable (drive) sleeve. In other embodiments, the rate of displacement may vary. For example, the piston rod may advance a large displacement per revolution to dispense a first amount of medicament from the cartridge and then a smaller displacement per revolution to dispense the rest of the cartridge. This is advantageous, as it can compensate for the fact that the first dose dispensed from the cartridge often has a lower volume than other doses, for a given displacement of the mechanism. If the pitch is equal on the threads of the housing and the piston rod, the piston rod advances a fixed amount for every revolution of the movable sleeve. However, if in an alternative embodiment the first turn of the thread on the piston rod has a large pitch and the other turns have a small pitch, during the first revolution the piston rod displacement depends on the large pitch of the first turn of thread on the piston rod, so it displaces a large amount per revolution. For subsequent revolutions the piston rod displacement depends on the smaller pitch of the piston rod thread, so it displaces a smaller amount. If, in a further embodiment, the housing thread has a larger pitch than the piston rod, during the first revolution, the piston rod displacement depends on the pitch of the housing thread, so it displaces a large amount per revolution. For subsequent revolutions the piston rod displacement depends on the pitch of the piston rod thread, so it displaces a smaller amount.

The aperture in the housing and/or the aperture in the gauge element may be a simple opening. However, it is preferred if at least one aperture is closed by a window or lens which prevents intrusion of dirt and/or may increase legibility of e.g. numbers on the number sleeve, for example due to a magnification.

According to a preferred embodiment of the disclosure the number sleeve is clipped to the housing at the distal end. This reduces the geometric tolerances for the gauge position. In other words, the number sleeve is preferably axially fixed relative to the housing but allowed to rotate relative thereto.

Preferably, the drive sleeve is clipped inside the number sleeve to retain it during subsequent assembly steps. In an alternative embodiment, the drive sleeve is clipped to the housing instead to retain it during subsequent assembly steps. In both embodiments, the drive sleeve is free to move beyond its assembled position when the button is pressed. The clips prevent movement in the disassembly direction, but do not prevent further movement, e.g. for dispense.

The lens and the window in the gauge may be incorporated into the housing using a 'twin-shot' moulding technology. For example, they are moulded during a 'first shot' in a translucent material, and the outer cover of the housing is moulded during a 'second shot' in an opaque material.

If there is only one threaded portion on the gauge element this reduces the length of this component.

Preferably, the tooth geometry on the clutch plate and the drive sleeve is chosen such that the dialing torque is low. Further, the clutch plate may comprise a dispense clicker which interferes with clicker teeth on the button.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39), des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, K or A, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Non-limiting, exemplary embodiments of the disclosure will now be described with reference to the accompanying drawings, in which.

DETAILED DESCRIPTION

Figure 1:
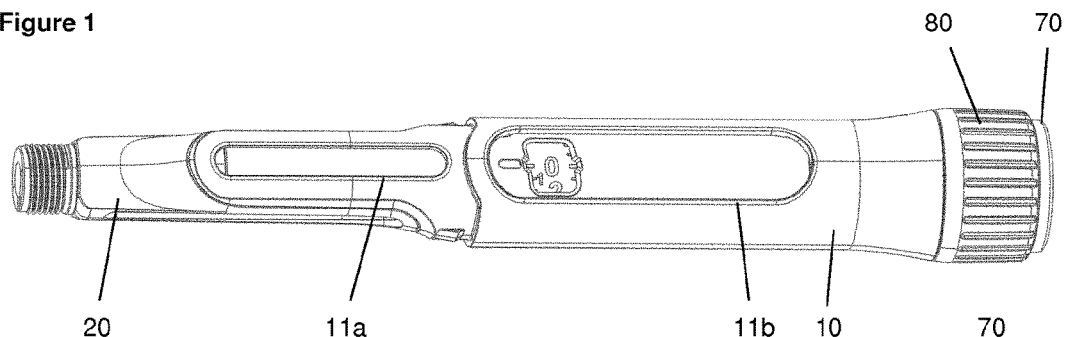
FIG. 1 shows a top view of the drug delivery device without monitoring device in the minimum dose position.
Figure 2:
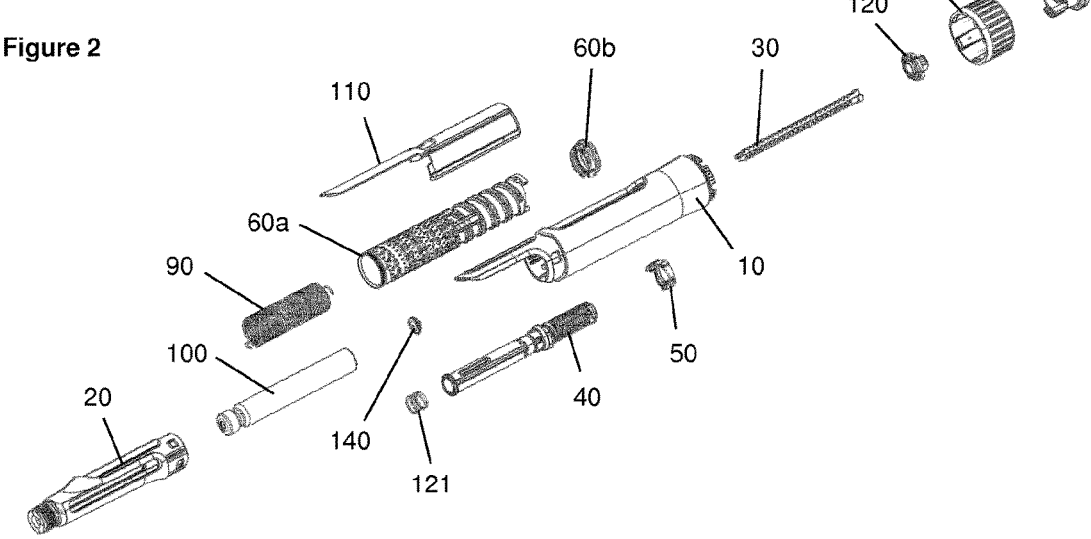
FIG. 2 shows an exploded view of the components of the device of FIG. 1.
Figure 3:
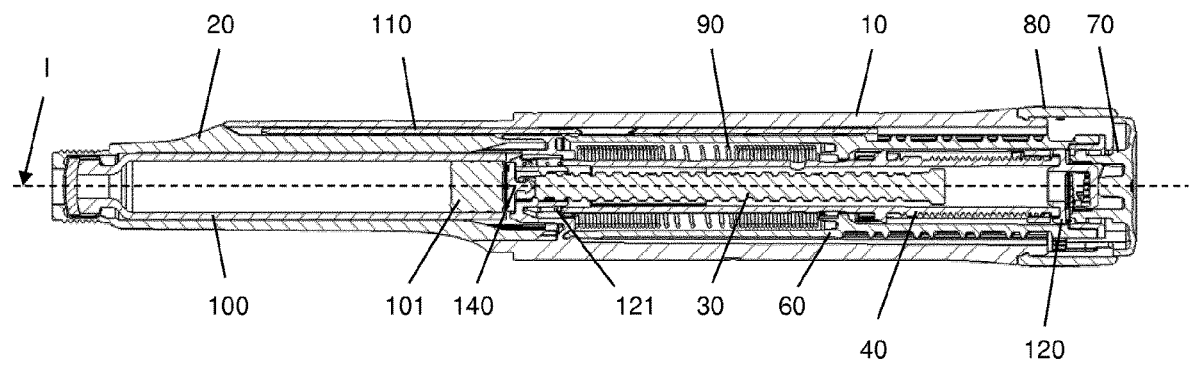
FIG. 3 shows a sectional view of the device of FIG. 2.

FIG. 1 shows a drug delivery device in the form of an injection pen. The device has a distal end (left end in FIG. 1) and a proximal end (right end in FIG. 1). The component parts of the drug delivery device are shown in FIG. 2. The drug delivery device comprises a body or housing 10, a cartridge holder 20, a lead screw (piston rod) 30, a drive sleeve 40, a nut 50, a dose indicator (number sleeve) 60, a trigger element in the form of a button 70, a dial grip or dose selector 80, a torsion spring 90, a cartridge 100, a gauge element 110, a clutch plate 120, a clutch spring 121 and a bearing 140. A needle arrangement (not shown) with a needle hub and a needle cover may be provided as additional components, which can be exchanged as explained above. All components are located concentrically about a common principal axis I of the mechanism which is shown in FIG. 3. In addition, a monitoring device 130 (not shown in FIGS. 1 to 3) may be attached e.g. to the button 70.

The housing 10 or body is a generally tubular element having a proximal end with an enlarged diameter. The housing 10 provides location for the liquid medication cartridge 100 and cartridge holder 20, windows 11a, 11b for viewing the dose number on the number sleeve 60 and the gauge element 110, and a feature on its external surface, e.g. a circumferential groove, to axially retain the dose selector 80. A flange-like or cylindrical inner wall comprises an inner thread engaging the piston rod 30. The housing 10 further has at least one internal, axially orientated slot or the like for axially guiding the gauge element 110. In the embodiment shown in the Figures, the distal end is provided with an axially extending strip partly overlapping cartridge holder 20. The Figures depict the housing 10 as a single housing component. However, the housing 10 could comprise two or more housing components which may be permanently attached to each other during assembly of the device.

The cartridge holder 20 is located at the distal side of housing 10 and permanently attached thereto. The cartridge holder may be a transparent or translucent component which is tubular to receive cartridge 100. The distal end of cartridge holder 20 may be provided with means for attaching a needle arrangement. A removable cap (not shown) may be provided to fit over the cartridge holder 20 and may be retained via clip features on the housing 10.

The piston rod 30 is rotationally constrained to the drive sleeve 40 via a splined interface. When rotated, the piston rod 30 is forced to move axially relative to the drive sleeve 40, through its threaded interface with the inner wall of housing 10. The lead screw 30 is an elongate member with an outer thread (FIG. 3) engaging the corresponding thread of the inner wall of housing 10. The leadscrew thread may have a large lead-in, for example a wedge shape form, at its distal end to engage a corresponding housing thread form on the first rotation. The interface comprises at least one longitudinal groove or track and a corresponding protrusion or spline of the driver 40. At its distal end, the lead screw 30 is provided with an interface for clip attachment of the bearing 140.

The drive sleeve 40 is a hollow member surrounding the lead screw 30 and arranged within number sleeve 60. It extends from an interface with the clutch plate 120 to an interface with the housing 10 and the clutch spring 121. The drive sleeve 40 is axially movable relative to the housing 10, the piston rod 30 and the number sleeve 60 in the distal direction against the axial bias of clutch spring 121 and in the opposite proximal direction under the axial bias of clutch spring 121.

A splined tooth interface with the housing 10 prevents rotation of the drive sleeve 40 during dose setting. This interface comprises for example a ring of radially extending outer teeth at the distal end of drive sleeve 40 and corresponding radially extending inner teeth of the housing component 10. When the button 70 is pressed, these drive sleeve 40 to housing 10 spline teeth are disengaged allowing the drive sleeve 40 to rotate relative to housing 10.

A further splined tooth interface with the number sleeve 60 is not engaged during dialing, but engages when the button 70 is pressed, preventing relative rotation between the drive sleeve 40 and number sleeve 60 during dispense. This interface may comprise inwardly directed splines on a flange on the inner surface of the number sleeve 60 and a ring of radially extending outer splines of drive sleeve 40. The corresponding splines are located on the number sleeve 60 and the drive sleeve 40, respectively, such that axial movement of the drive sleeve 40 relative to the (axially fixed) number sleeve 60 engages or disengages the splines to rotationally couple or decouple the drive sleeve 40 and the number sleeve 60. Preferably, the splines are arranged such that they are decoupled when teeth of drive sleeve 40 and inner teeth of housing component 10 mesh and engage when teeth and inner teeth disengage.

A further interface of the drive sleeve 40 comprises a ring of ratchet teeth located at the proximal end face of drive sleeve 40 and a ring of corresponding ratchet teeth of clutch plate 120.

The driver 40 has a threaded section providing a helical track for the nut 50. In addition, a last dose abutment or stop is provided which may be the end of the thread track or preferably a rotational hard stop for interaction with a corresponding last dose stop of nut 50, thus limiting movement of the nut 50 on the driver thread. At least one longitudinal spline engages a corresponding track of the lead screw 30. Further, the drive sleeve is provided with a ramp interacting with a clicker arm when the drive sleeve 40 is in its distal position during dose dispensing, i.e. when button 70 is depressed.

Figure 6:
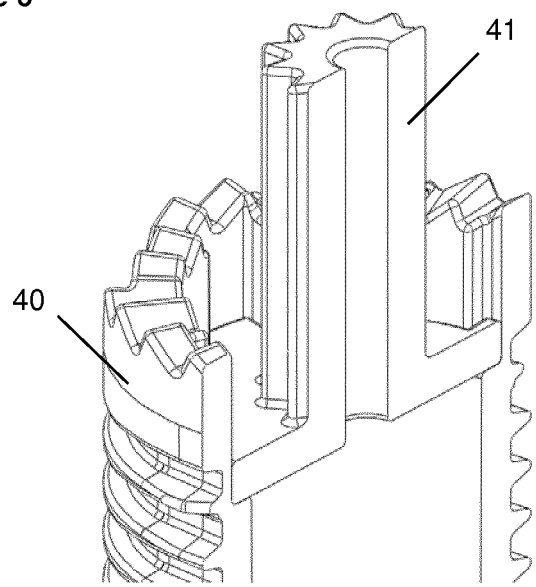
FIG. 6 shows an enlarged sectional view of a detail of the device of FIG. 4.

The driver 40 comprises an indicator 41 in the form of a central elongate pinion as shown in FIG. 6 with teeth to be viewed by a monitoring device 130. The indicator 41 may be a separate component rigidly fixed to the driver 40 or may be a unitary part thereof. In the exemplary embodiment of FIG. 6, the indicator 41 is rigidly fixed to drive sleeve 40 by spline features ensuring that the drive sleeve 40 and the indicator 41 rotate together. The same features may also ensure that these two parts move axially together. The indicator 41 provides features that can be viewed by the monitoring device 130 to determine whether the drive sleeve 40 is rotating. The example of the elongate pinion shape of the indicator 41 uses tooth-shaped protrusions that can be viewed, but other methods may be used, including printing on the proximal end surface.

The last dose nut 50 is located between the number sleeve 60 and the drive sleeve 40. It is rotationally constrained to the number sleeve 60, via a splined interface. It moves along a helical path relative to the drive sleeve 40, via a threaded interface, when relative rotation occurs between the number sleeve 60 and drive sleeve 40 which is during dialing only. As an alternative, the nut 50 may be splined to the driver 40 and threaded to the number sleeve 60. A last dose stop is provided engaging a stop of drive sleeve 40 when a dose is set corresponding to the remaining dispensable amount of medicament in the cartridge 100.

Figure 7:
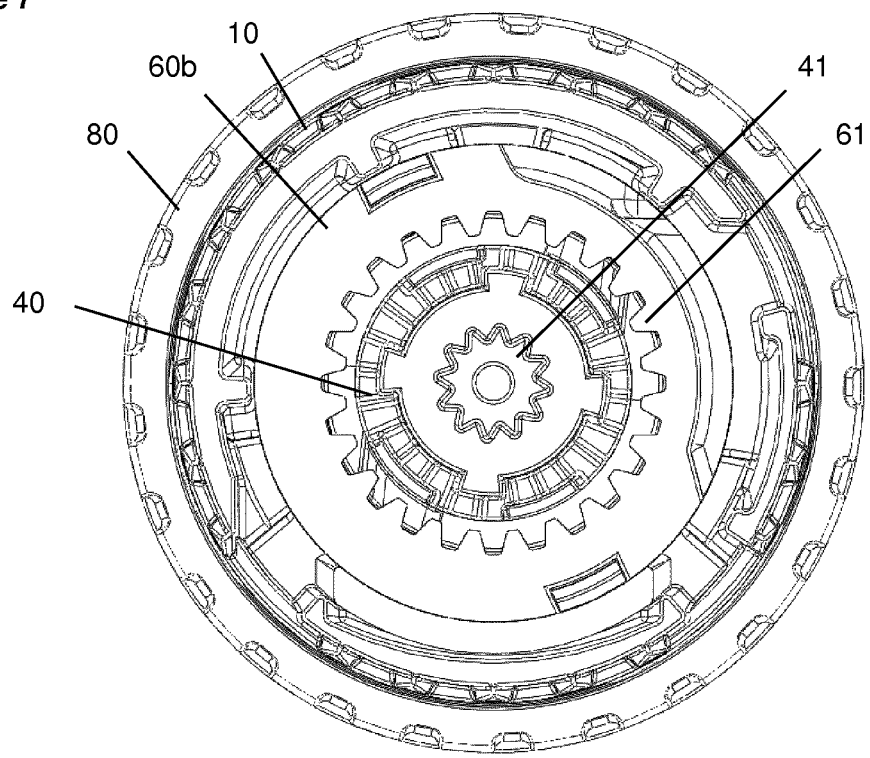
FIG. 7 shows a view on the proximal end of the device of FIG. 4 with clutch plate and button removed.

The dose setting member or number sleeve 60 is a tubular element as shown in FIGS. 2 and 3. The number sleeve 60 is rotated during dose setting (via dose selector 80) and dose correction and during dose dispensing by torsion spring 90. Together with gauge element 110 the number sleeve 60 defines a zero position ('at rest') and a maximum dose position. Thus, the number sleeve 60 may be seen as a dose setting member. As can be seen in FIG. 7, the number sleeve 60 comprises a ring of splines 61 or teeth which are visible from the proximal end of the device when the clutch plate 120 and the button 70 are removed. Further, splines 61 are visible for the monitoring device 130 if the button 70 and the clutch plate 120 are transparent or translucent or are provided with apertures.

For manufacturing reasons the number sleeve 60 of the embodiment shown in the Figures comprises a number sleeve lower 60a which is rigidly fixed to a number sleeve upper 60b during assembly to form the number sleeve 60. Number sleeve lower 60a and number sleeve upper 60b are separate components only to simplify number sleeve 60 mould tooling and assembly. As an alternative, the number sleeve 60 may be a unitary component. The number sleeve 60 is constrained to the housing 10 by features towards the distal end to allow rotation but not translation. The number sleeve lower 60a is marked with a sequence of numbers, which are visible through the gauge element 110 and the openings 11a, 11b in the housing 10, to denote the dialed dose of medicament.

Further, the number sleeve lower 60a has a portion with an outer thread engaging the gauge element 110. End stops are provided at the opposite ends of this thread to limit relative movement with respect to the gauge element 110.

The dose selector 80 is axially constrained to the housing 10. It is rotationally constrained, via the splined interface, to the button 70. This splined interface which includes grooves interacting with spline features formed by the annular skirt of button 70 remains engaged irrespective of the dose button 70 axial positions. The dose selector 80 or dose dial grip is a sleeve-like component with a serrated outer skirt. The button 70 may be transparent or translucent to allow the monitoring device 130 (when attached to the button) viewing internal component parts of the device. In addition or as an alternative, one or more apertures may be provided in the button 70.

The torsion spring 90 is attached at its distal end to the housing 10 and at the other end to the number sleeve 60. The torsion spring 90 is located inside the number sleeve 60 and surrounds a distal portion of the drive sleeve 40. The torsion spring 90 may be pre-wound upon assembly, such that it applies a torque to the number sleeve 60 when the mechanism is at zero units dialed. The action of rotating the dose selector 80, to set a dose, rotates the number sleeve 60 relative to the housing 10, and charges the torsion spring 90 further.

The torsion spring 90 is formed from a helical wire with at least two different pitches. Both ends are formed from 'closed' coils, i.e. the pitch equals the wire diameter and each coil contacts the adjacent coil. The central portion has 'open' coils, i.e. the coils do not contact each other.

The cartridge 100 is received in cartridge holder 20 (FIG. 3). The cartridge 100 may be a glass ampoule having a moveable rubber bung 101 at its proximal end. The distal end of cartridge 100 is provided with a pierceable rubber seal which is held in place by a crimped annular metal band. In the embodiment depicted in the Figures, the cartridge 100 is a standard 1.5 ml cartridge. The device is designed to be disposable in that the cartridge 100 cannot be replaced by the user or health care professional. However, a reusable variant of the device could be provided by making the cartridge holder 20 removable and allowing backwinding of the lead screw 30 and the resetting of nut 50.

The gauge element 110 is constrained to prevent rotation but allow translation relative to the housing 10 via a splined interface. The gauge element 110 has a helical feature on its inner surface which engages with the helical thread cut in the number sleeve 60 such that rotation of the number sleeve 60 causes axial translation of the gauge element 110. This helical feature on the gauge element 110 also creates stop abutments against the end of the helical cut in the number sleeve 60 to limit the minimum and maximum dose that can be set.

The gauge element 110 has a generally plate or band like component having a central aperture or window and two flanges extending on either side of the aperture. The flanges are preferably not transparent and thus shield or cover the number sleeve 60, whereas the aperture or window allows viewing a portion of the number sleeve lower 60a. Further, gauge element 110 has a cam and a recess interacting with the clicker arm of the number sleeve 60 at the end of dose dispensing.

The clutch plate 120 is a ring-like component. The clutch plate 120 is splined to the number sleeve 60. It is also coupled to the drive sleeve 40 via a ratchet interface. The ratchet provides a detented position between the number sleeve 60 and drive sleeve 40 corresponding to each dose unit, and engages different ramped tooth angles during clockwise and anti-clockwise relative rotation. A clicker arm is provided on the clutch plate 120 for interaction with ratchet features of the button 70. The clutch plate 120 may be transparent or translucent to allow the monitoring device 130 (when attached to the button) to view internal component parts of the device. In addition or as an alternative, one or more apertures may be provided in the clutch plate 120.

Figure 4:
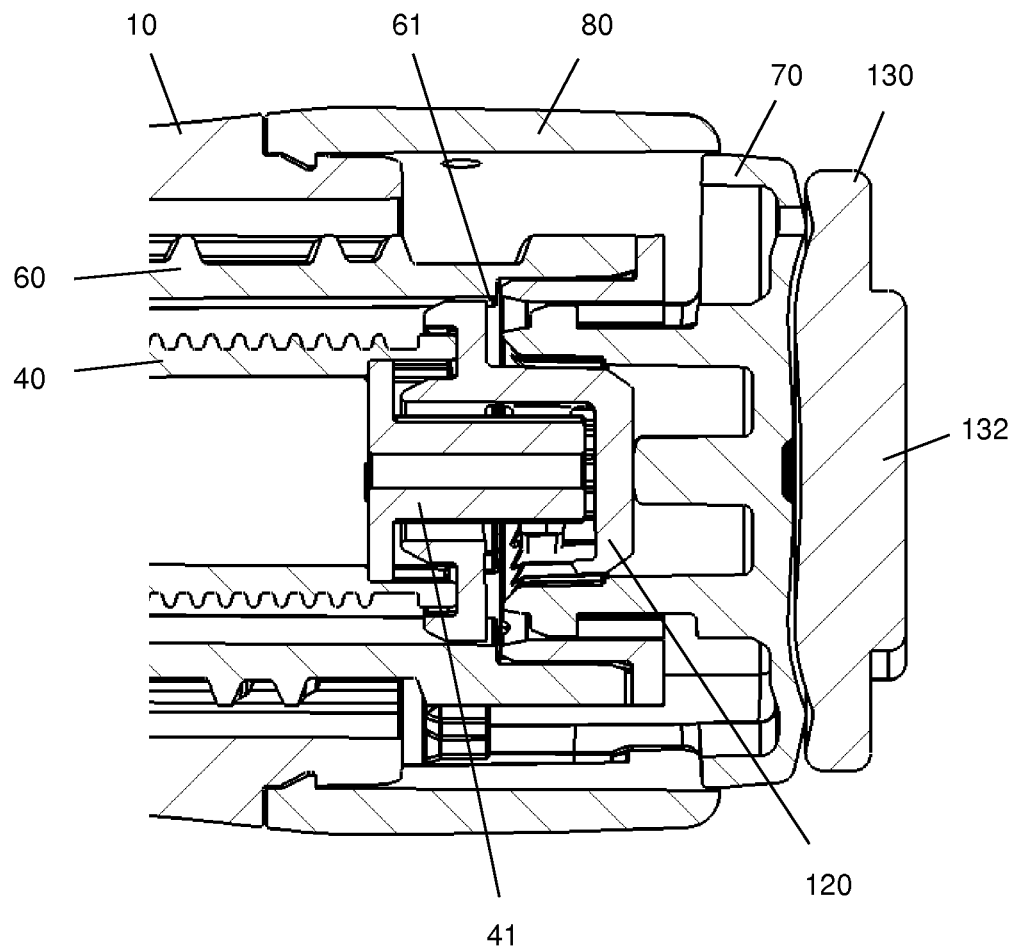
FIG. 4 shows a sectional view of the proximal end of the drug delivery device of the present disclosure.
Figure 5:
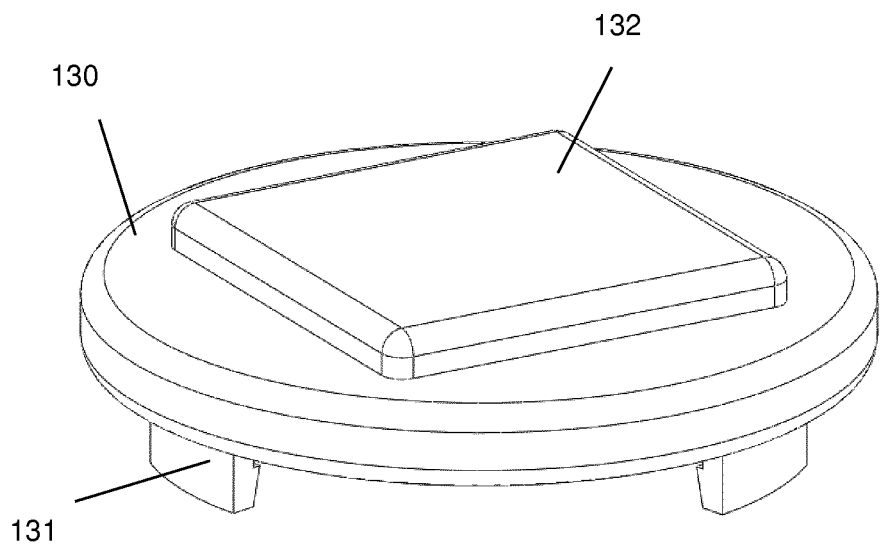
FIG. 5 shows a monitoring device attachable to the drug delivery device of FIG. 1.

The monitoring device 130 is depicted in FIGS. 4 and 5 as a component part which may be clipped onto the proximal end of button 70, for example in a releasable manner. Monitoring device 130 may comprise clips 131 for attachment on the button 70, a display 132. Further, it comprises a data processor, an optical detector and an energy source, which are all not visible in FIGS. 4 and 5.

The bearing 140 is axially constrained to the piston rod 30 and acts on the bung 101 within the liquid medicament cartridge. It is axially clipped to the lead screw 30, but free to rotate.

With the device in the 'at rest' condition as shown in FIG. 6, the number sleeve 60 is positioned against its zero dose abutment with the gauge element 110 and the button 70 is not depressed. Dose marking '0' on the number sleeve 60 is visible through the windows of the housing 10 and gauge element 110, respectively. The torsion spring 90, which has a number of pre-wound turns applied to it during assembly of the device, applies a torque to the number sleeve 60 and is prevented from rotating by the zero dose abutment.

The user selects a variable dose of liquid medicament by rotating the dose selector 80 clockwise, which generates an identical rotation in the number sleeve 60. Rotation of the number sleeve 60 causes charging of the torsion spring 90, increasing the energy stored within it. As the number sleeve 60 rotates, the gauge element 110 translates axially due to its threaded engagement thereby showing the value of the dialed dose. The gauge element 110 has flanges either side of its window area which cover the numbers printed on the number sleeve 60 adjacent to the dialed dose to ensure only the set dose number is made visible to the user.

A specific feature of this disclosure is the inclusion of a visual feedback feature in addition to the discrete dose number display typical on devices of this type. The distal end (flange) of the gauge element 110 creates a sliding scale through the small window 11a in the housing 10. As an alternative, the sliding scale could be formed using a separate component engaged with the number sleeve 60 on a different helical track.

As a dose is set by the user, the gauge element 110 translates axially, the distance moved proportional to the magnitude of the dose set. This feature gives clear feedback to the user regarding the approximate size of the dose set. The dispense speed of an auto-injector mechanism may be higher than for a manual injector device, so it may not be possible to read the numerical dose display during dispense. The gauge feature provides feedback to the user during dispense regarding dispense progress without the need to read the dose number itself. For example, the gauge display may be formed by an opaque element on the gauge element 110 revealing a contrasting coloured component underneath. Alternatively, the revealable element may be printed with coarse dose numbers or other indices to provide more precise resolution. In addition, the gauge display simulates a syringe action during dose set and dispense.

The openings 11a, 11b in the housing 10 allow the user to view the gauge feature and number display. To reduce dust ingress and prevent the user from touching moving parts, these openings 11a, 11b are covered by translucent windows. These windows may be separate components, but in this embodiment they are incorporated into the housing 10 using 'twin-shot' moulding technology.

The mechanism utilises a dose selector 80 with an increased diameter relative to the housing 10 which aids dialing although this is not a requirement of the mechanism. This feature is particularly useful (but not essential) for an auto-injector mechanism where a power supply is charged during dose setting and the torque required to turn the dose selector 80 may be higher than for a non-auto injector device.

The drive sleeve 40 is prevented from rotating as the dose is set and the number sleeve 60 rotated, due to the engagement of its splined teeth with teeth of the housing 10. Relative rotation must therefore occur between the clutch plate 120 and drive sleeve 40 via the ratchet interface.

The user torque required to rotate the dose selector 80 is a sum of the torque required to wind up the torsion spring 90, and the torque required to overhaul the ratchet interface. The clutch spring 121 is designed to provide an axial force to the ratchet interface and to bias the clutch plate 120 onto the drive sleeve 40. As the user rotates the dose selector 80 sufficiently to increment the mechanism by one increment, the number sleeve 60 rotates relative to the drive sleeve 40 by one ratchet tooth. At this point the ratchet teeth re-engage into the next detented position. An audible click is generated by the ratchet re-engagement, and tactile feedback is given by the change in torque input required.

Relative rotation of the number sleeve 60 and the drive sleeve 40 is allowed as splines are disengaged during dose setting. This relative rotation also causes the last dose nut 50 to travel along its threaded path, towards its last dose abutment on the drive sleeve 40. With no user torque applied to the dose selector 80, the number sleeve 60 is now prevented from rotating back under the torque applied by the torsion spring 90, solely by the ratchet interface between the clutch plate 120 and the drive sleeve 40. The user may now choose to increase the selected dose by continuing to rotate the dose selector 80 in the clockwise direction. If the user continues to increase the selected dose until the maximum dose limit is reached, the number sleeve 60 engages with its maximum dose abutment on the maximum dose abutment of gauge element 110. This prevents further rotation of the number sleeve 60, clutch plate 120 and dose selector 80.

Depending on how many increments have already been delivered by the mechanism, during selection of a dose, the last dose nut 50 may contact its last dose abutment with stop face of the drive sleeve 40. The abutment prevents further relative rotation between the number sleeve 60 and the drive sleeve 40, and therefore limits the dose that can be selected. The position of the last dose nut 50 is determined by the total number of relative rotations between the number sleeve 60 and drive sleeve 40, which have occurred each time the user sets a dose.

With the mechanism in a state in which a dose has been selected, the user is able to deselect any number of increments from this dose. Deselecting a dose is achieved by the user rotating the dose selector 80 anti-clockwise. The torque applied to the dose selector 80 by the user is sufficient, when combined with the torque applied by the torsion spring 90, to overhaul the ratchet interface between the clutch plate 120 and drive sleeve 40 in the anti-clockwise direction. When the ratchet is overhauled, anti-clockwise rotation occurs in the number sleeve 60 (via the clutch plate 120), which returns the number sleeve 60 towards the zero dose position, and unwinds the torsion spring 90. The relative rotation between the number sleeve 60 and drive sleeve 40 causes the last dose nut 50 to return along its helical path, away from the last dose abutment.

With the mechanism in a state in which a dose has been selected, the user is able to activate the mechanism to commence delivery of a dose. Delivery of a dose is initiated by the user depressing the button 70 axially in the distal direction. When the button 70 is depressed, splines between the button 70 and number sleeve 60 are disengaged, rotationally disconnecting the button 70 and dose selector 80 from the delivery mechanism, i.e. from number sleeve 60, gauge element 110 and torsion spring 90. Splines on the button 70 engage with splines on the housing 10, preventing rotation of the button 70 (and hence the dose selector 80) during dispense. As the button 70 is stationary during dispense, it can be used in the dispense clicker mechanism. A stop feature in the housing 10 limits axial travel of the button 70 and reacts any axial abuse loads applied by the user, reducing the risk of damaging internal components.

The clutch plate 120 and drive sleeve 40 travel axially with the button 70. This engages the splined tooth interface between the drive sleeve 40 and number sleeve 60 preventing relative rotation between the drive sleeve 40 and number sleeve 60 during dispense. The splined tooth interface between the drive sleeve 40 and the housing 10 disengages, so the drive sleeve 40 can now rotate and is driven by the torsion spring 90 via the number sleeve 60, and clutch plate 120.

Rotation of the drive sleeve 40 causes the piston rod 30 to rotate due to their splined engagement, and the piston rod 30 then advances due to its threaded engagement to the housing 10. The number sleeve 60 rotation also causes the gauge element 110 to traverse axially back to its zero position whereby the zero dose abutment stops the mechanism.

Delivery of a dose continues via the mechanical interactions described above while the user continues to depress the button 70. If the user releases the button 70, the clutch spring 121 returns the drive sleeve 40 to its 'at rest' position (together with the clutch plate 120 and button 70), engaging the splines between the drive sleeve 40 and housing 10, preventing further rotation and stopping dose delivery.

During delivery of a dose, the drive sleeve 40 and number sleeve 60 rotate together, so that no relative motion in the last dose nut 50 occurs. The last dose nut 50 therefore travels axially relative to the drive sleeve 40 during dialing only.

At the end of dose dispensing, additional audible feedback is provided in the form of a 'click', distinct from the 'clicks' provided during dispense, to inform the user that the device has returned to its zero position via the interaction of the clicker arm on the number sleeve 60 with the ramp on the drive sleeve 40 and the cam and the recess on the gauge element 110. This embodiment allows feedback to only be created at the end of dose delivery and not created if the device is dialed back to, or away from, the zero position.

The monitoring device 130 may be used as a dwell timer detecting different kinds of movements including rotation and linear displacement and outputting a feedback signal to a user. In the embodiment of FIGS. 4 to 7, the dwell timer 130 monitors rotation of the number sleeve 60 (by monitoring splines 61), and the drive sleeve 40 (by monitoring indicator 41). These two component parts are both stationary when at rest. During dialing, the number sleeve 60 rotates relative to the housing 10 and together with button 70 onto which the monitoring device 130 is attached, while the drive sleeve 40 is still stationary. During dispensing, the number sleeve 60 and the drive sleeve 40 rotate together relative to the housing 10, while the button 70 (and with it the monitoring device 130) is rotationally constrained to the stationary housing 10.

After detection of the end of dose dispensing, the data processor may cause the display 132 to output a feedback signal with a delay corresponding to the dwell period. As an alternative, the feedback signal may be generated throughout the dwell period and may terminate or change at the end of the dwell period. In addition or as an alternative to the feedback signal of the display 132, a tactile (e.g. vibration) and/or audible signal may be generated by the monitoring device 130.

Further, the monitoring device 130 may be configured for detecting a pressure exerted to button 70 which exceeds a dose dispensing start threshold. Thus, a warning signal may be provided if the device is jammed or otherwise malfunctioning. In addition, the monitoring device 130 may be configured to provide a user with a feedback signal at the end of dose dispensing, i.e. when the dwell period starts, in a dose dispensing aborting or blocking condition, and/or when dose dispensing starts with an overdose or underdose dial setting. The latter case requires inputting data regarding the correct dose into the monitoring device 130.

REFERENCE NUMERALS 10 housing
11a opening (window)
11b opening (window)

20 cartridge holder
30 lead screw (piston rod)
40 driver (axially movable drive sleeve)
41 indicator
50 nut
60 dose indicator (number sleeve)
60a number sleeve lower
60b number sleeve upper
61 splines
70 button
80 dose selector
90 torsion spring
100 cartridge
101 bung
110 gauge element
120 clutch plate
121 clutch spring
130 monitoring device
131 clip
132 display
140 bearing
l longitudinal axis

The invention claimed is:

1. A drug delivery device for selecting and dispensing a number of user variable doses of a medicament, the drug delivery device comprising:
   a housing;
   a monitoring device;
   a dose setting member rotatable relative to the housing during dose setting and during dose dispensing;
   a driver rotationally constrained to the housing during dose setting and rotatable together with the dose setting member during dose dispensing; and
   an at least partially translucent or transparent button;
   wherein the dose setting member and the driver move relative to each other during dose setting or during dose dispensing and the relative movement of the dose setting member and the driver during dose setting differs from the relative movement of the dose setting member and the driver during dose dispensing,
   wherein the at least partially translucent or transparent button is configured to allow optical detection, by the monitoring device, of the movements of the dose setting member and the driver relative to the housing, relative to the monitoring device, or relative to each other during dose setting or during dose dispensing.

2. The drug delivery device according to claim 1, wherein the dose setting member and the driver move relative to each other during dose setting and during dose dispensing.

3. The drug delivery device according to claim 1, wherein at least one of the dose setting member or the driver is at least partially translucent or transparent.

4. The drug delivery device according to claim 1, wherein at least one of the dose setting member or the driver comprises an indicator portion configured to be optically detected by the monitoring device to monitor the movements of the dose setting member and the driver relative to the housing, relative to the monitoring device, and relative to each other during dose setting and during dose dispensing.

5. The drug delivery device according to claim 1, further comprising at least one of a lead screw, a dial grip, a spring, a gauge element, or a clutch.

6. The drug delivery device according to claim 5, wherein the at least one of the lead screw, the dial grip, the spring, the gauge element, or the clutch is at least partially translucent or transparent.

7. The drug delivery device according to claim 5, wherein the monitoring device is configured to monitor at least one of the following motions:
   a) rotation of the dose setting member relative to the monitoring device and/or relative to the housing during dose setting and/or dose dispensing,
   b) rotation of the driver relative to the monitoring device and/or relative to the housing during dose setting and/or dose dispensing,
   c) rotation of the dose setting member relative to the driver during dose setting and/or dose dispensing,
   d) return of the dose setting member and/or the driver to an at rest position,
   e) rotation of the button relative to the monitoring device and/or relative to the housing during dose setting and/or dose dispensing, or
   f) rotation of the lead screw, the clutch and/or the dial grip relative to the monitoring device and/or relative to the housing during dose setting and/or dose dispensing.

8. The drug delivery device according to claim 7, wherein the monitoring device comprises an optical detector, a data processor, and at least one output member for providing an optical, tactile, and/or audible feedback to a user of the drug delivery device, and wherein the data processor is configured as a dwell timer for outputting the optical, tactile, and/or audible feedback to a user of the drug delivery device via the at least one output member at a predefined time span after detection of an end of at least one of the motions a) to f).

9. The drug delivery device according to claim 5, further comprising an at least partially translucent or transparent clutch interposed between the dose setting member and the driver.

10. The drug delivery device according to claim 5, further comprising an at least partially translucent or transparent clutch interposed between the dose setting member and the button.

11. The drug delivery device according to claim 1, wherein one or more of the dose setting member or the driver has a non-circular rotation indicator portion.

12. The drug delivery device according to claim 11, wherein the non-circular rotation indicator portion faces toward the monitoring device.

13. The drug delivery device according to claim 1, wherein one or more of the dose setting member or the driver have an optically detectable surface coding.

14. The drug delivery device according to claim 13, wherein the optically detectable surface coding faces toward the monitoring device.

15. The drug delivery device according to claim 1, wherein the button is transparent or translucent for visible light or opaque for visible light but transparent or translucent for invisible light.

16. The drug delivery device according to claim 1, wherein the monitoring device is releasably attached to the housing.

17. The drug delivery device according to claim 1, wherein the monitoring device is releasably attached to the housing and to at least one further component part of the drug delivery device.

18. The drug delivery device according to claim 1, wherein the monitoring device comprises an optical detector, a data processor, and at least one output member for providing an optical, tactile, and/or audible feedback to a user of the drug delivery device.

19. The drug delivery device according to claim 18, wherein the monitoring device is configured for detecting a button pressure exceeding a dose dispensing start threshold, and/or wherein the monitoring device is configured to provide a user with a feedback signal in one or more of the following events:
- a) an end of dose dispensing,
- b) a dose dispensing aborting or blocking condition, or
- c) a dose dispensing starting with an overdose or underdose dial setting.

20. The drug delivery device according to claim 1, wherein the monitoring device is configured to display a size of a dialed dose, indicate whether the drug delivery device is dialing or dispensing, during dispensing show the size of the remaining dose and/or to store a history of the size and time of doses that have been dispensed, and display the history of the size and time of doses that have been dispensed on a screen or allow downloading of data to an external device.

21. The drug delivery device according to claim 1, further comprising a cartridge containing a medicament.

* * * * *

UNITED STATES PATENT AND TRADEMARK OFFICE
CERTIFICATE OF CORRECTION

Page 1 of 1

PATENT NO. : 11,090,436 B2
APPLICATION NO. : 15/557338
DATED : August 17, 2021
INVENTOR(S) : Avery et al.

It is certified that error appears in the above-identified patent and that said Letters Patent is hereby corrected as shown below:

On the Title Page

Item (72), Column 1, Line 3, under "Inventors:", delete "Meredith"

Item (72), Column 1, Line 7, under "Inventors:", delete "Keir"

Item (72), Column 1, Line 8, under "Inventors:", delete "Frederick"

In the Claims

Column 26, Line 30, Claim 9, delete "claim 5," and insert -- claim 1, --

Column 26, Line 34, Claim 10, delete "claim 5," and insert -- claim 1, --

Signed and Sealed this
Second Day of November, 2021

Drew Hirshfeld
*Performing the Functions and Duties of the*
*Under Secretary of Commerce for Intellectual Property and*
*Director of the United States Patent and Trademark Office*